(12) United States Patent
Kobayashi et al.

(10) Patent No.: US 9,072,436 B2
(45) Date of Patent: Jul. 7, 2015

(54) DEVICE FOR MEASURING INFORMATION REGARDING BLOOD PRESSURE

(75) Inventors: Tatsuya Kobayashi, Otsu (JP); Hideaki Yoshida, Kyoto (JP)

(73) Assignee: OMRON HEALTHCARE Co., Ltd., Kyoto (JP)

( * ) Notice: Subject to any disclaimer, the term of this patent is extended or adjusted under 35 U.S.C. 154(b) by 541 days.

(21) Appl. No.: 13/044,231

(22) Filed: Mar. 9, 2011

(65) Prior Publication Data

US 2011/0160599 A1    Jun. 30, 2011

Related U.S. Application Data

(63) Continuation of application No. PCT/JP2009/065595, filed on Sep. 7, 2009.

(30) Foreign Application Priority Data

Sep. 26, 2008    (JP) .................................. 2008-248279

(51) Int. Cl.
*A61B 5/02* (2006.01)
*A61B 5/0225* (2006.01)
(Continued)

(52) U.S. Cl.
CPC ........... *A61B 5/0225* (2013.01); *A61B 5/02141* (2013.01); *A61B 5/02* (2013.01); *A61B 5/021* (2013.01); *A61B 8/04* (2013.01)

(58) Field of Classification Search
CPC ........... A61B 5/02233; A61B 5/02225; A61B 5/0225; A61B 5/022; A61B 5/02208; A61B 8/04; A61B 5/02141; A61B 5/02; A61B 5/021; A61B 5/04; A61M 1/3639

USPC .................................. 600/301, 481, 489–499
See application file for complete search history.

(56) References Cited

U.S. PATENT DOCUMENTS 5,423,324 A *   6/1995  Tomita ........................... 600/493
6,336,901 B1 *   1/2002  Itonaga et al. .................. 600/499
(Continued)

FOREIGN PATENT DOCUMENTS

JP              2877951         1/1999
JP           2004-113593 A      4/2004
(Continued)

OTHER PUBLICATIONS

Office Action issued in corresponding Chinese Application No. 200980135695.1 dated Aug. 31, 2012, with English translation thereof (11 pages).
(Continued)

*Primary Examiner* — Jacqueline Cheng
*Assistant Examiner* — Puya Agahi
(74) *Attorney, Agent, or Firm* — Osha Liang LLP

(57) ABSTRACT

A measurement device includes an air bag on a peripheral side, an air bag on a central side, and an air bag positioned therebetween. During blood pressure measurement, the air bags integrally behave, and the blood pressure is measured from the change in inner pressure thereof. During pulse wave measurement, the inner pressure of the air bag on the peripheral side is maintained to higher than or equal to the systolic blood pressure, and the measurement site is avascularized. The inner pressure of the air bag on the central side is maintained to the pressure near the blood pressure value, and the pulse wave is measured from the change in inner pressure thereof. The inner pressure of the air bag positioned therebetween is opened to atmospheric pressure, and the vibration of the air bag on the central side is prevented from propagating to the air bag on the peripheral side.

1 Claim, 7 Drawing Sheets

(51) Int. Cl.
*A61B 5/021* (2006.01)
*A61B 8/04* (2006.01)

(56) References Cited

U.S. PATENT DOCUMENTS

| 6,694,821 | B2* | 2/2004 | Yamakoshi et al. | 73/756 |
| 2003/0109788 | A1* | 6/2003 | Ogura | 600/490 |
| 2009/0124913 | A1* | 5/2009 | Yamashita et al. | 600/499 |
| 2010/0010357 | A1* | 1/2010 | Ostrowiecki | 600/499 |
| 2010/0106031 | A1* | 4/2010 | Souma | 600/494 |

FOREIGN PATENT DOCUMENTS

| JP | 2006-334153 | 12/2006 |
| JP | 2007-44362 | 2/2007 |
| JP | 2009-112429 | 5/2009 |

OTHER PUBLICATIONS

Patent Abstracts of Japan for Japanese Publication No. 2009-112429, Publication date May 28, 2009 (1 page).
Patent Abstracts of Japan for Japanese Publication No. 2006-334153, Publication date Dec. 14, 2006 (1 page).
Patent Abstracts of Japan for Japanese Publication No. 2007-044362, Publication date Feb. 22, 2007 (1 page).
Patent Abstracts of Japan for Japanese Publication No. 2004-113593, Publication date Apr. 15, 2004 (1 page).
International Search Report for International Application No. PCT/JP2009/065595, mailed on Oct. 6, 2009 (5 pages).

* cited by examiner

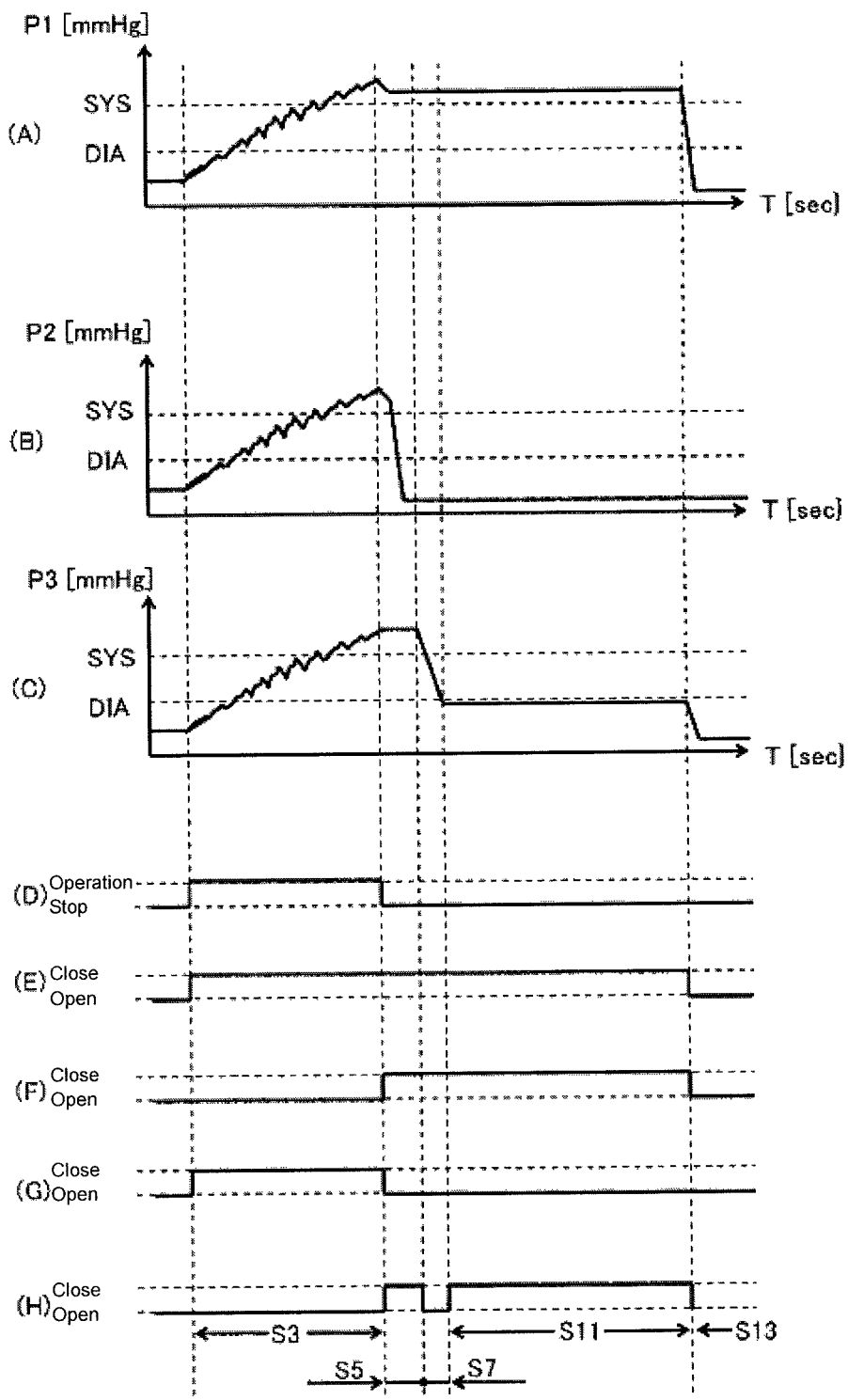

DEVICE FOR MEASURING INFORMATION REGARDING BLOOD PRESSURE

TECHNICAL FIELD

The present invention relates to blood pressure information measurement devices, and in particular, to a blood pressure information measurement device for measuring blood pressure information using a cuff that internally includes a plurality of fluid bags.

BACKGROUND ART

Measuring blood pressure information such as blood pressure and pulse wave is useful in determining the degree of arterial sclerosis.

For instance, Japanese Unexamined Patent Publication No. 2004-113593 (patent document 1) discloses a technique of separating the ejection wave ejected from the heart and the reflection wave from the iliac artery branch portion and the sclerosis site in the artery while avascularizing the peripheral side, and determining the degree of arterial sclerosis from their amplitude difference, the amplitude ratio, the appearance time difference, and the like.

Japanese Unexamined Patent Publication No. 2007-044362 (patent document 2) discloses a technique of arranging a cuff for measuring the pulse wave immediately below the blood pressure cuff, and measuring the pulse wave propagation speed to the relevant cuff.

Patent document 1: Japanese Unexamined Patent Publication No. 2004-113593
Patent document 2: Japanese Unexamined Patent Publication No. 2007-044362
Patent document 3: Japanese Unexamined Patent Publication No. 2006-334153

SUMMARY OF INVENTION

In the technique disclosed in patent document 1, however, if the cuff for suppressing the blood flow and the cuff for measuring the pulse wave are contacting each other, the noise from the other cuff mixes and determination of high accuracy may not be made. A space thus needs to be provided between the cuffs.

Japanese Unexamined Patent Publication No. 2006-334153 (patent document 3) discloses a technique in which a plate-shaped member is arranged between the pressurization cuff and the pulse wave cuff. The cuff for suppressing the blood flow and the cuff for measuring the pulse wave can be arranged in series by adopting the technique of patent document 3. However, if the cuffs are arranged in such a manner, the cuff width becomes long as a whole, and measurement may become difficult using such cuff if the measurement site is the upper arm for people having a short upper arm length. The cuff size of the blood pressure is also known to influence the accuracy of the blood pressure measurement. Thus, it is difficult to substitute a narrow blood pressure cuff for people having a short upper arm length.

Patent document 2 can measure the degree of arterial sclerosis at the upper arm site, but the degree of arterial sclerosis of other sites cannot be calculated.

Therefore, one or more embodiments of the present invention provides a measurement device capable of obtaining blood pressure information with which an accurate index of arterial sclerosis can be calculated without lengthening the width of the cuff.

According to one or more embodiments of the present invention, a blood pressure information measurement device in which an airbag including three or more adjacent air bags is arranged such that the adjacent air bags are closely attached to each other in a direction from a central side towards a peripheral side when a cuff including the air bag is attached to a measurement site, the blood pressure information measurement device including an inner pressure adjustment unit for adjusting an inner pressure of the air bag; a connection unit for connecting or disconnecting each of the three or more adjacent air bags and the inner pressure adjustment unit; a control unit for controlling the inner pressure of each of the three or more air bags by controlling the connection state by the connection unit and the inner pressure adjustment in the inner pressure adjustment unit; and a measurement unit for acquiring blood pressure information based on change in inner pressure of the air bag, wherein the measurement unit calculates a blood pressure value as the blood pressure information based on the change in the inner pressure of the air bag by a first control in the control unit, and acquires a pulse wave waveform as the blood pressure information based on the change in the inner pressure of the air bag by a second control in the control unit.

According to one or more embodiments of the present invention, an accurate index of arterial sclerosis is calculated by using the blood pressure information obtained in the measurement device.

BRIEF DESCRIPTION OF THE DRAWINGS

FIG. 7 is a view showing the pressure change in each air bag and the operation of each unit during the measurement operation in the measurement device according to an embodiment of the present invention.

DETAILED DESCRIPTION OF INVENTION

Figure 1:
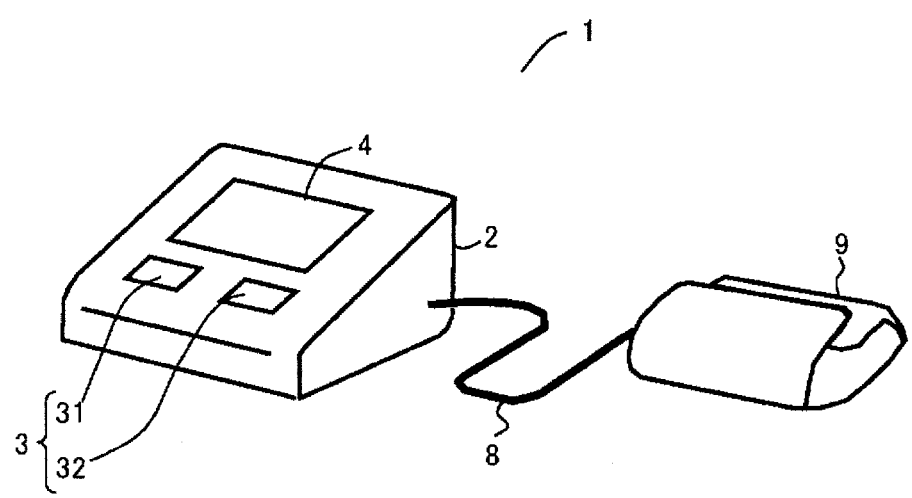
FIG. 1 is a perspective view showing a specific example of an outer appearance of a measurement device according to an embodiment of the present invention.

Embodiments of the present invention will be hereinafter described with reference to the drawings. The same reference numerals denote the same components and configuring elements in the following description. The names and functions thereof are the same.

A blood pressure information measurement device (hereinafter referred to as measurement device) 1 according to one or more embodiments of the present invention will be described using FIG. 1. In the following description, the "blood pressure information" refers to information related to blood pressure that is obtained by measuring the living body.

Specific examples of the "blood pressure information" include blood pressure value, pulse wave waveform, heart rate, and the like.

With reference to FIG. 1, the measurement device 1 includes a base body 2 and an arm band 9 connected to the base body 2 and attached to the upper arm or the measurement site, which are connected with an air tube 8. A display unit 4 for displaying various information including the measurement result and an operation unit 3 operated when giving various instructions to the measurement device 1 are arranged on the front surface of the base body 2. The operation unit 3 includes a switch 31, which is operated to turn ON/OFF the power supply, and a switch 32, which is operated to instruct start of the measurement.

Figure 2:
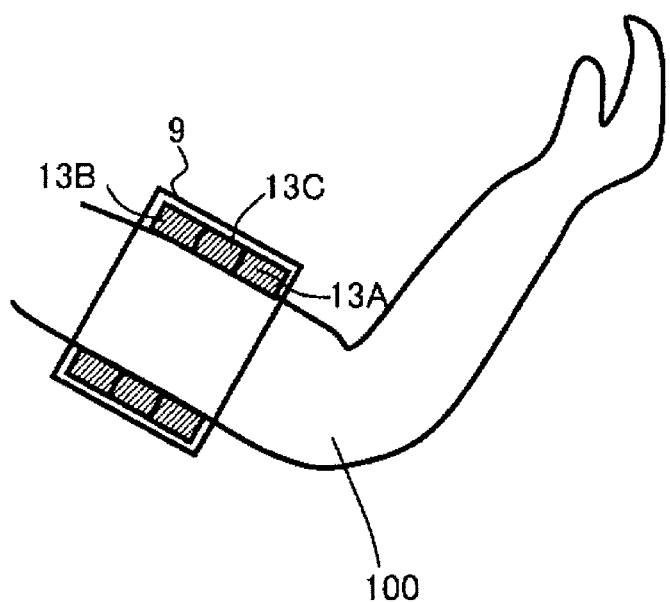
FIG. 2 is a schematic cross-sectional view showing the measurement posture when measuring the blood pressure information using the measurement device according to an embodiment of the present invention.

With reference to FIG. 2, the arm band 9 is wrapped around an upper arm 100, which is the measurement site, to measure the pulse wave using the measurement device 1. The switch 32 is then pushed in such state, so that the blood pressure information is measured with the measurement device 1. With reference to FIG. 2, the arm band 9 includes an air bag serving as a fluid bag for compressing the living body and measuring the blood pressure and the pulse wave serving as the blood pressure information. The air bag includes an air bag 13A, an air bag 13B, and an air bag 13C. The air bag 13A, the air bag 13B, and the air bag 13C are all arranged along the width direction of the arm band 9 so as to closely attach in the direction along the artery in such order when the arm band 9 is attached to the upper arm 100 or the measurement site. In other words, the air bag 13A is arranged on the arm band 9 so as to be on the side closest to the wrist, that is, the peripheral side, when the arm band 9 is attached to the upper arm or the measurement site. The air bag 13B is arranged on the arm band 9 so as to be on the side farthest from the wrist, that is, the central side, when the arm band 9 is attached to the upper arm or the measurement site. The air bag 13C is arranged at an intermediate position between the air bag 13A and the air bag 13B. The ratio of the length in the width direction of the arm band 9 of the air bags 13A, 13C, 13B is preferably 1:1:1.

Figure 3:
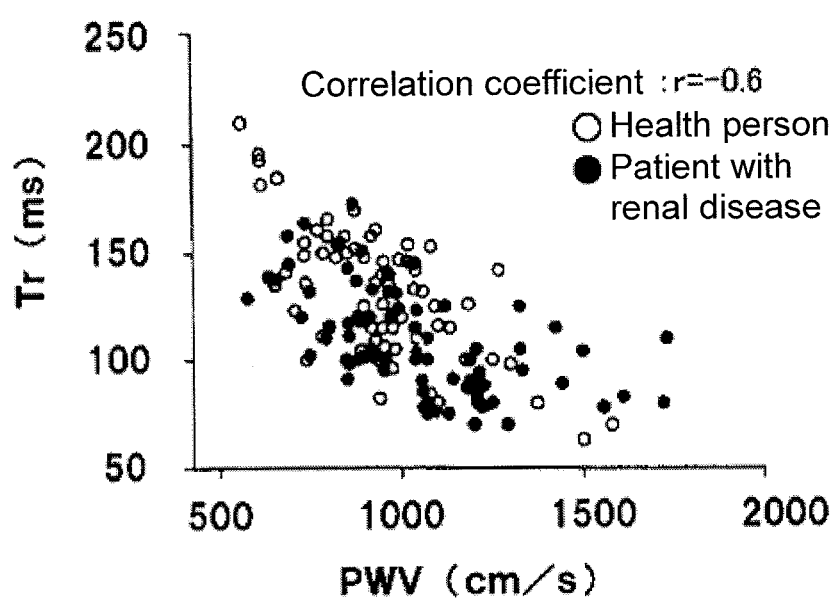
FIG. 3 is a view showing a specific example of the correlation of the appearance time difference Tr between the ejection wave and the reflection wave and the PWV.

The measurement device 1 obtains the index for determining the degree of arterial sclerosis based on the pulse wave waveform serving as the blood pressure information obtained from one measurement site. As the speed of propagation of the pulse wave ejected from the heart (hereinafter referred to as PWV: Pulse Wave Velocity) becomes faster as the arterial sclerosis advances, the PWV acts as an index for determining the degree of arterial sclerosis. In one or more embodiments, the appearance time difference Tr between the ejection wave and the reflection wave reflected and returned from the branch portion of the iliac artery is obtained as an index for determining the degree of arterial sclerosis. When the measurement site is the upper arm and the reflection wave is the reflection wave from an ankle serving as the peripheral, the correlation between the appearance time difference Tr and the PWV is statistically obtained as shown in, for example, FIG. 3 if the individual parameters such as height and sex are obtained, as described in the document "Hypertension 1992 July; 20(1)" by London G M et al., (published on Jul. 20, 1992) P. 10 to 19. Therefore, the appearance time difference Tr between the ejection wave and the reflection wave can be an index for determining the degree of arterial sclerosis.

Figure 4:
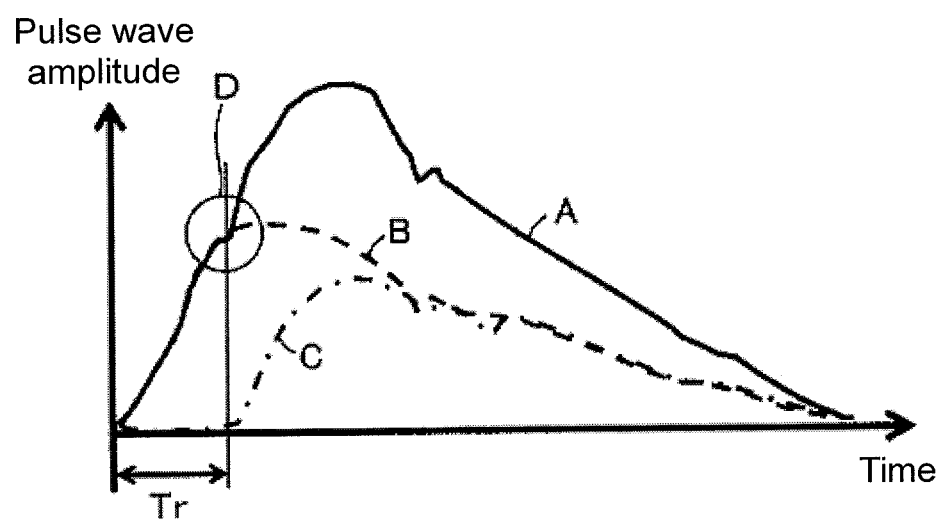
FIG. 4 is a view describing the relationship of the measured pulse wave waveform, the ejection wave, and the reflection wave.

The principle for obtaining the index for determining the degree of arterial sclerosis based on the pulse wave waveform obtained from one measurement site will be described using FIG. 4. In FIG. 4, the waveform A shown with a solid line indicates the measured pulse wave waveform. The waveform B shown with a broken line indicates the ejection wave, and the waveform C shown with a chain dashed line indicates the reflection wave. As shown in FIG. 4, the pulse wave waveform A obtained by measurement is a synthetic wave of the ejection wave B and the reflection wave C. The arrival of the reflection wave to the measurement site is detected as an inflection point D in the pulse wave waveform A. Therefore, the appearance time difference Tr is obtained in the time from the rise of the pulse wave waveform A to the inflection point D. An accurate pulse wave waveform needs to be obtained in order to obtain the inflection point D from the pulse wave waveform A obtained by measurement. An accurate PWV can be obtained using the correlation shown in FIG. 3 by obtaining an accurate pulse wave waveform.

The function configuration of the measurement device 1 will be described using FIG. 5. The measurement device 1 includes an inner pressure adjustment mechanism connected to the air bags 13A, 13B, 13C with the air tube 8, a connection adjustment mechanism for adjusting the connection state of the air bags 13A, 13B, 13C and the inner pressure adjustment mechanism, and a control mechanism for controlling such mechanisms.

Figure 5:
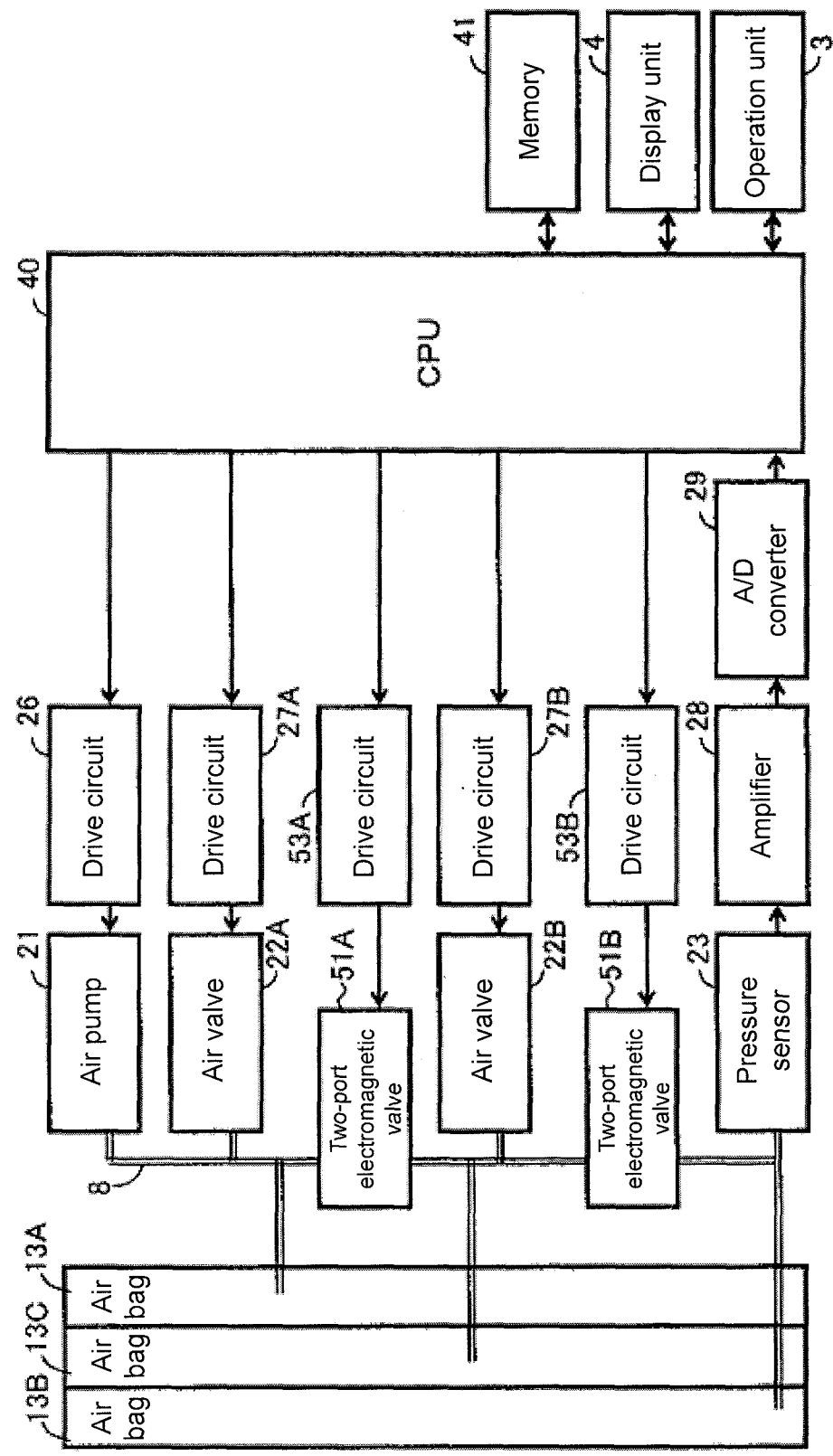
FIG. 5 is a block diagram showing functions of the measurement device according to an embodiment of the present invention.

With reference to FIG. 5, the measurement device 1 includes an air pump 21 and an air valve 22A connected to the air bag 13A through the air tube 8, and drive circuits 26, 27A for respectively driving the same. An air valve 22B connected to the air bag 13C through the air tube 8 and a drive circuit 27B for driving the air valve 22B are also arranged. A pressure sensor 23 connected to the air bag 13B through the air tube 8 is also arranged. The air pump 21, the air valve 22A, and the air valve 22B are connected with interposing a two-port electromagnetic valve 51A therebetween, and the air valve 22B and the pressure sensor 23 are connected with interposing a two-port electromagnetic valve 51B therebetween. In other words, the air bag 13A is directly connected to the air pump 21 and the air valve 22A with the air tube 8, connected to the air valve 22B with interposing the two-port electromagnetic valve 51A therebetween, and connected to the pressure sensor 23 with interposing the two-port electromagnetic valve 51A and the two-port electromagnetic valve 51B therebetween. Furthermore, the air bag 13C is directly connected to the air valve 22B with the air tube 8, connected to the air pump 21 and the air valve 22A with interposing the two-port electromagnetic valve 51A therebetween, and connected to the pressure sensor 23 with interposing the two-port electromagnetic valve 51B therebetween. The air bag 13B is directly connected to the pressure sensor 23 with the air tube 8, connected to the air valve 22B with interposing the two-port electromagnetic valve 51B therebetween, and connected to the air pump 21 and the air valve 22A with interposing the two-port electromagnetic valve 51A and the two-port electromagnetic valve 51B therebetween.

The drive circuits 26, 27A, 27B, 53A, 53B are connected to a CPU (Central Processing Unit) 40, and operate according to a control signal from the CPU 40. The CPU 40 controls the drive circuits 26, 27A, 27B, 53A, 53B based on a command input to the operation unit 3 arranged at the base body 2 of the measurement device. The measurement result is output to the display unit 4 and a memory 41. The memory 41 stores measurement results and programs executed by the CPU 40.

The inner pressure adjustment mechanism includes the air pump 21, the drive circuit 26 thereof, the air valves 22A, 22B, the drive circuits 27A, 27B thereof, and the pressure sensor 23. The connection adjustment mechanism includes the two-port electromagnetic valves 51A, 51B and the drive circuits 53A, 53B thereof. The control mechanism includes the CPU 40.

The air pump 21 is driven by the drive circuit 26 that received the command from the CPU 40, and sends compressed gas to the air bags 13A, 13B, 13C. The air pump 21 thereby pressurizes the air bags 13A, 13B, 13C.

The open/close state of the air valves 22A, 22B is controlled by the drive circuits 27A, 27B that received the command from the CPU 40. The pressure in the air bags 13A, 13B, 13C is controlled when the open/close state of the air valves 22A, 22B is controlled. The air valves 22A, 22B thereby maintain or depressurize the pressure of the air bags 13A, 13B, 13C.

The pressure sensor 23 detects the pressure in the air bags 13A, 13B, 13C. The pressure sensor 23 outputs a pressure signal, which is a signal corresponding to a detection value, to an amplifier 28. The amplifier 28 amplifies the signal input from the pressure sensor 23, and outputs to an A/D converter 29. The A/D converter 29 digitalizes the pressure signal, which is an analog signal input from the amplifier 28, and outputs to the CPU 40.

The two-port electromagnetic valves 51A, 51B are respectively connected to the drive circuits 53A, 53B, and the open/close state of the valves is controlled by the circuits. Specifically, the two-port electromagnetic valve 51A includes a valve for connecting or disconnecting the side of the air pump 21, the air valve 22A and the air bag 13A, and the side of the air valve 22B and the air bag 13C. The connection state is controlled by driving the valve with the drive circuit 53A. The two-port electromagnetic valve 51B includes a valve for connecting or disconnecting the side of the air valve 22B and the air bag 13C, and the side of the pressure sensor 23 and the air bag 13B. The connection state is controlled by driving the valve with the drive circuit 53B.

The measurement operation in the measurement device 1 will be described using FIG. 6. The operation shown in FIG. 6 starts when the subject and the like push the measurement button provided in the operation unit 3 of the base body 2, and is realized when the CPU 40 reads out the program stored in the memory 41 and controls each unit shown in FIG. 6. FIGS. 7A to 7C each shows the pressure change in each of the air bags 13A, 13B, 13C during the measurement operation in the measurement device 1. In other words, FIG. 7A shows the temporal change of the inner pressure P1 of the air bag 13A, FIG. 7B shows the temporal change of the inner pressure P2 of the air bag 13C, and FIG. 7C shows the temporal change of the inner pressure P3 of the air bag 13B. FIGS. 7D to 7H each shows the operation state of each unit during the measurement operation in the measurement device 1. In other words, FIG. 7D shows the operation of the air pump 21, FIG. 7E shows the temporal change of the open/close state of the air valve 22A, FIG. 7F shows the temporal change of the open/close state of the two-port electromagnetic valve 51A, FIG. 7G shows the temporal change of the open/close state of the air valve 22B, and FIG. 7H shows the temporal change of the open/close state of the two-port electromagnetic valve 51B. S3 to S13 given on the time axis in FIG. 7 coincides with each operation in the measurement device 1, to be described later.

Figure 6:
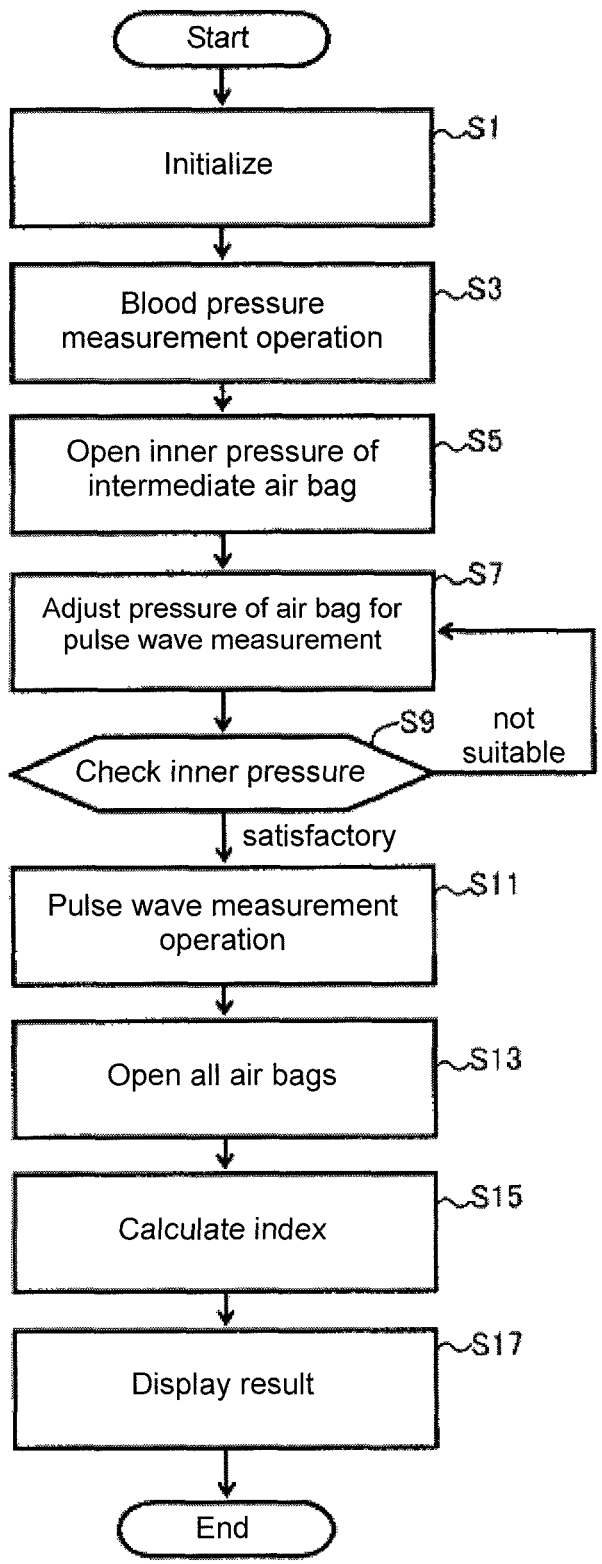
FIG. 6 is a flowchart showing the measurement operation in the measurement device according to an embodiment of the present invention.

With reference to FIG. 6, when the measurement operation starts, the initialization of each unit is carried out in the CPU 40 in step S1, and the blood pressure measurement operation is carried out in step S3. Specifically, in step S3, the CPU 40 first outputs a control signal for opening the two-port electromagnetic valves 51A, 51B to the drive circuits 27A, 27B. The two-port electromagnetic valves 51A, 51B are thereby opened during the period of step S3, as shown in FIGS. 7F and 7H. The CPU 40 also outputs a control signal for closing the air valves 22A, 22B to the drive circuits 27A, 27B. The air valves 22A, 22B are thereby closed during the period of step S3, as shown in FIGS. 7E and 7G.

When the two-port electromagnetic valves 51A, 51B are opened and the air valves 22A, 22B are closed, one closed space including the air bags 13A, 13B, 13C connected to the air tube 8, the air pump 21, the air valves 22A, 22B, and the pressure sensor 23 is configured. The CPU 40 then outputs a control signal for operating the air pump 21 to the drive circuit 26 with the closed space configured. The air pump 21 thereby operates during the period of step S3, as shown in FIG. 7D. When air is supplied to the closed space including the air bags 13A, 13B, 13C by the air pump 21, the air is supplied into the air bags 13A, 13B, 13C, and the respective inner pressure P1, P2, P3 is increased as shown in FIG. 7A to 7C. As the pressure sensor 23 is connected to the closed space, the pressure sensor 23 outputs a pressure signal corresponding to the inner pressure of the closed space equal to all inner pressures P1, P2, P3 of the air bags 13A, 13B, 13C.

According to the above connection state, the air bags 13A, 13B, 13C integrally function as an air bag for blood pressure measurement in time of the blood pressure measurement. In step S3, the CPU 40 calculates the systolic blood pressure value and the diastolic blood pressure value based on the pressure signal obtained from the pressure sensor 23 in the increasing process of the inner pressures P1, P2, P3.

After the systolic blood pressure value is obtained in the increasing process of the inner pressures P1, P2, P3 as a result of the operation in step S3, the CPU 40 terminates the blood pressure measurement operation and opens the inner pressure of the air bag 13C in step S5. Specifically, the CPU 40 first outputs a control signal for stopping the operation of the air pump 21 to the drive circuit 26 in step S5. The operation of the air pump 21 is then stopped during the period of step S5, as shown in FIG. 7D. The CPU 40 also outputs a control signal for closing the two-port electromagnetic valves 51A, 51B to the drive circuits 27A, 27B. The two-port electromagnetic valves 51A, 51B are thereby closed during the period of step S5, as shown in FIGS. 7F and 7H.

When the two-port electromagnetic valves 51A, 51B are closed, three closed spaces, a first closed space including the air bag 13A connected to the air tube 8, the air pump 21, and the air valve 22A, a second closed space including the air bag 13B and the pressure sensor 23, and a third closed space including the air bag 13C and the air valve 22B are configured. The CPU 40 then outputs a control signal for opening the air valve 22B to the drive circuit 27B with three closed spaces configured. The control signal is not output to the drive circuit 27A. The air valve 22A is then continued to be closed and the air valve 22B is opened during the period of step S5, as shown in FIGS. 7E and 7G. When the air valve 22B is opened with the three closed spaces configured, the inner pressure P1 of the air bag 13A equal to the inner pressure of the first closed space including the air valve 22A and the inner pressure P3 of the air bag 13B equal to the inner pressure of the second closed space maintain the inner pressure higher than the systolic blood pressure value or the final inner pressure of the period of step S5 and the period of step S3, as shown in FIGS. 7A and 7C. The inner pressure P2 of the air bag 13C equal to the inner pressure of the third space including the air valve 22B is decreased until reaching the atmospheric pressure in the period of step S5, as shown in FIG. 7B.

After the inner pressure P2 of the air bag 13C is decreased to the atmospheric pressure in step S5, the CPU 40 decreases and adjusts the inner pressure P3 of the air bag 13B to become the pressure suited for pulse wave measurement in step S7. Specifically, the CPU 40 outputs a control signal for opening the two-port electromagnetic valve 51B to the drive circuit 53B with the three spaces configured in step S7. The two-port electromagnetic valve 51B is then opened, and the second space including the air bag 13B and the third space including the air bag 13C of the three spaces are connected thereby forming a new space. Since the air valve 22B is opened in step S5, the inner pressure P3 of the air bag 13B is decreased towards the atmospheric pressure in the period of step S7, as shown in FIG. 7C. In step S7, the CPU 40 monitors the inner pressure P3 of the air bag 13B based on the pressure signal obtained from the pressure sensor 23, and continues depressurization until the inner pressure reaches a pressure suited for measurement of the pulse wave. The inner pressure suited for measurement of the pulse wave is the pressure around the diastolic blood pressure, as shown in FIG. 7C. At the time point the inner pressure P3 of the air bag 13B reached the inner pressure suited for the measurement of the pulse wave ("satisfactory" in step 9), the CPU 40 terminates the adjustment operation of the inner pressure P3 of the air bag 13B, and performs the pulse wave measurement operation of step S11.

Specifically, when completing the adjustment operation of the inner pressure P3 of the air bag 13B and performing the pulse wave measurement operation in step S11, the CPU 40 outputs a control signal for closing the two-port electromagnetic valve 51B to the drive circuit 53B. The new space is then separated to the second space and the third space, and the three spaces are configured in the period of step S11, similar to the period of step S5.

As shown in FIGS. 7E and 7F, the two-port electromagnetic valve 51A maintains the closed state in step S5 and the air valve 22A maintains the closed state in step S3 in the period of step S11, and thus, the inner pressure P1 of the air bag 13A equal to the inner pressure of the first closed space is maintained at the inner pressure higher than the systolic blood pressure value or the final inner pressure of the period of step S3 in the period of step S11, as shown in FIG. 7A. As a result, the air bag 13A avascularize the measurement site. As shown in FIGS. 7G and 7H, the two-port electromagnetic valve 51B is closed and the air valve 22B maintains the open state in step S5 in the period of step S11, and thus, the inner pressure P2 of the air bag 13C equal to the inner pressure of the third closed space is maintained at the atmospheric pressure or the final inner pressure of the period of step S5 in the period of step S11, as shown in FIG. 7B. As shown in FIG. 7H, the second space including the air bag 13B and the pressure sensor 23 is a closed space since the two-port electromagnetic valve 51B is closed in the period of step S11, and the pressure sensor 23 outputs a pressure signal corresponding to the inner pressure of the second closed space equal to the inner pressure P3 of the air bag 13B.

According to such connection state, the air bag 13B functions as an air bag for pulse wave measurement, the air bag 13A functions as an air bag for avascularization, and the air bag 13C functions as a space between the air bag 13A and the air bag 13B. In step S11, the CPU 40 obtains a pulse wave waveform based on the pressure signal obtained from the pressure sensor 23. The pulse wave measurement operation in step S11 is carried out for a predetermined time.

After the pulse wave measurement of step S11 is completed, in step S13, the CPU 40 outputs a control signal to the drive circuits 27A, 27B to open the air valves 22A, 22B, and releases the inner pressures P1, P2, P3 of the air bags 13A, 13C 13B to atmospheric pressure.

In step S15, the CPU 40 calculates the appearance time difference Tr between the ejection wave and the reflection wave serving as an index for determining the degree of arterial sclerosis from the pulse wave waveform obtained in step S11. A specific calculation method in step S15 is not limited to a specific method, but, for example, the above mentioned inflection point D may be obtained by calculating the multi-order derivation (e.g., fourth-order derivation) of the obtained pulse wave waveform, and the time to the inflection point D from the rise of the obtained pulse wave waveform may be read to obtain the appearance time difference Tr between the ejection wave and the reflection wave.

In step S17, the CPU 40 performs a process for displaying the measurement result such as the calculated systolic blood pressure (SYS) and the diastolic blood pressure (DIA), the measured pulse wave and the like, the index calculated in step S15, and the like on the display unit 4 arranged in the base body 2, and displays the measurement result.

As described above, the air bag 13B is used as the air bag for measurement, and the air bag 13A is used as the air bag for avascularization at the time of pulse wave measurement in the measurement device 1. In this case, the inner pressure P2 of the air bag 13C positioned between the air bag 13A and the air bag 13B is opened to the atmospheric pressure at the time of the pulse wave measurement of step S11, and hence, the air bag 13C functions as the gap between the air bag 13A and the air bag 13B, and the air bag 13A and the air bag 13B operate as separate bodies. The transmission of the vibration generated in the air bag 13B, which becomes a noise at the time of pulse wave measurement, to the air bag 13A is greatly suppressed. The accuracy of the pulse wave measurement thus can be enhanced, and a useful index for determining the degree of arterial sclerosis can be obtained.

Furthermore, as the connection state of the air bags 13A, 13B, 13C and the inner pressure adjustment mechanism is adjusted by the connection adjustment mechanism, the air bags 13A, 13B, 13C are integrally used as the blood pressure measurement air bag at the time of the blood pressure measurement of step S3, and the air bag 13B is used as the pulse wave measurement air bag at the time of the pulse wave measurement of step S11. That is, at the time of the blood pressure measurement, the volume of the air bag 13B used for the pulse wave measurement can be suppressed since the air bags 13A, 13C are also used in addition to the air bag 13B. As a result, the increase of the volume from the usual blood pressure measurement air bag can be suppressed. Specifically, since the width of the air bag 13A is ⅓, the width of the air bag 13B is ⅓, and the width of the air bag 13C is ⅓ of the width of the usual blood pressure measurement air bag, the blood pressure and the pulse wave can be measured at the same width as the usual blood pressure measurement air bag, that is, the same volume. The enlargement of the entire device thus can be suppressed. The load with respect to the subject then can be suppressed.

Furthermore, the pulse wave vibration absorbed by the air in the air bag 13B can be suppressed by suppressing the volume of the air bag 13B used for the pulse wave measurement. As a result, the measurement accuracy of the pulse wave can be enhanced. A useful index for determining the degree of arterial sclerosis also can be obtained.

The connection state of the air bags 13A, 13B, 13C and the inner pressure adjustment mechanism is adjusted by the connection adjustment mechanism, and the inner pressure adjustment mechanism is connected to the air bag that requires inner pressure adjustment. The inner pressure adjustment mechanism thus does not need to be mounted for every air bag. This also contributes to miniaturization, lighter weight, and lower cost of the device.

In the above example, three air bags, that is, the air bag on the central side used for the measurement at the time of the pulse wave measurement, the air bag on the peripheral side used for the avascularization, and the air bag therebetween, which are closely attached continuously in the direction of the artery, are arranged on the arm band 9 in the measurement device 1. However, the number of air bags is not limited to three, and may be four or more, in which a plurality of air bags may exist between the air bag for pulse wave measurement and the air bag for avascularization.

The embodiments disclosed herein are illustrative in all aspects and should not be construed as being restrictive. The scope of the invention is defined by the claims rather than by the description made above, and meanings equivalent to the claims and all modifications within the scope are intended to be encompassed therein.

DESCRIPTION OF SYMBOLS 1 measurement device
2 base body
3 operation unit
4 display unit
5 measurement unit
8 air tube
9 arm band
13A, 13B, 13C air bag
21 air pump
22A, 22B air valve
23 pressure sensor
26, 27A, 27B, 53A, 53B drive circuit
28 amplifier
29 A/D converter
31, 32 switch
40 CPU
41 memory
51A, 51B two-port electromagnetic valve
100 upper arm

The invention claimed is:

1. A blood pressure information measurement device comprising:
   a fluid bad including a first air bag, a second air bag, and a third air bag, said fluid bag arranged such that the three air bags are independently pressure controlled and are closely attached to each other in a direction from a peripheral side, which is closest to a wrist being measured, towards a central side, which is furthest from the wrist being measured, when a cuff including the fluid bag is attached to a measurement site;
   an inner pressure adjustment unit including an air pump, a first air valve connected to the first air bag and a second air valve connected to the second air bag for adjusting an inner pressure of the fluid bag;
   a connection unit including a first two-port electromagnetic valve connected between the first air bag and the second air bag, and a second two-port electromagnetic valve connected between the second air bag and the third air bag, each of said first and second two-port electromagnetic valves being configured to switch between a connection state and a disconnection state;
   a control unit for controlling the inner pressure of each of the air bags by controlling the inner pressure adjustment unit and the connection unit; and
   a measurement unit for acquiring blood pressure information based on a change in the inner pressure of the fluid bag,
   wherein the control unit performs, as a first control, a control for changing the respective inner pressure of the air bags at a same pressure such that the first air valve and the second air valve are closed and, at a same time, the three air bags are connected to each other through the first and second two-port electromagnetic valves, which are both in the connection state, and
   wherein the control unit performs, as a second control, a control for changing the respective inner pressure of the three air bags at different pressures such that the first air valve is maintained closed and the first two-port electromagnetic valve is turned to the disconnection state to set the first air bag at a first predetermined pressure, the second air valve is opened to set the second air bag at a second predetermined pressure that is less than the first predetermined pressure, and the second two-port electromagnetic valve is controlled between the disconnection state and the connection state to set the third air bag at a third predetermined pressure that is between the first and second predetermined pressures, and
   wherein the measurement unit calculates a blood pressure value as the blood pressure information based on the change in the inner pressure of the fluid bag by the first control in the control unit, and acquires a pulse wave waveform as the blood pressure information based on the change in the inner pressure of the fluid bag by the second control in the control unit.

* * * * *